United States Patent [19]
Kraatz et al.

[11] Patent Number: 4,783,474

[45] Date of Patent: Nov. 8, 1988

[54] HALOGENOALKYL-, ALKENYL- AND ALKINYL-AZOLES

[75] Inventors: Udo Kraatz, Leverkusen; Wolfgang Behrenz, Overath; Carl Fedtke, Cologne, all of Fed. Rep. of Germany

[73] Assignee: Bayer Aktiengesellschaft, Leverkusen, Fed. Rep. of Germany

[21] Appl. No.: 104,710

[22] Filed: Oct. 2, 1987

Related U.S. Application Data

[63] Continuation-in-part of Ser. No. 885,046, Jul. 14, 1986, abandoned.

[30] Foreign Application Priority Data

Jul. 20, 1985 [DE] Fed. Rep. of Germany ....... 3525978
Jan. 14, 1987 [DE] Fed. Rep. of Germany ....... 3700916

[51] Int. Cl.$^4$ .................. C07D 249/08; C07D 233/54; A01N 43/653; A01N 43/50

[52] U.S. Cl. .................................... 514/383; 514/184; 514/399; 514/396; 548/101; 548/262; 548/341

[58] Field of Search ........................ 548/341, 262, 101; 514/383, 399, 521

[56] References Cited

U.S. PATENT DOCUMENTS

| | | | |
|---|---|---|---|
| 3,860,632 | 1/1975 | Martin et al. | 560/22 |
| 4,104,399 | 8/1978 | Pommer et al. | 548/262 |
| 4,315,017 | 2/1982 | Linhart et al. | 548/262 |
| 4,463,014 | 7/1984 | Martel et al. | 514/521 |
| 4,517,201 | 5/1985 | Kerry et al. | 574/521 |

FOREIGN PATENT DOCUMENTS

| | | | |
|---|---|---|---|
| 3417468 | 11/1985 | Fed. Rep. of Germany | 548/262 |
| 3525978 | 1/1987 | Fed. Rep. of Germany . | |
| 0015002 | 9/1980 | United Kingdom . | |
| 0089920 | 9/1983 | United Kingdom . | |
| 0160931 | 11/1985 | United Kingdom . | |

OTHER PUBLICATIONS

Research Disclosure, Jun. 1982, #21844.
Gasparini et al, J. Organomet. Chem 1980 (88(2), pp. 141-150, CA93:26499q (Reg #74045-50-4).

*Primary Examiner*—Richard L. Raymond
*Assistant Examiner*—D. L. Dinner
*Attorney, Agent, or Firm*—Sprung Horn Kramer & Woods

[57] ABSTRACT

Novel halogenoalkyl-, alkenyl- and alkinyl-azoles of the formula

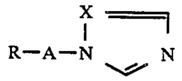

in which
X represents a nitrogen atom or a CH grouping,
R represents optionally substituted tert.-alkyl or optionally substituted cycloalkyl, and
A represents one of the groupings —C≡C—,

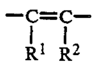
or
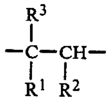

in which
$R^1$ represents halogen, alkoxy or trialkylsilyloxy,
$R^2$ represents hydrogen or halogen, and
$R^3$ represents halogen, and acid and metal salt addition products thereof synergize insecticides and herbicides which function by photosynthesis inhibition.

9 Claims, No Drawings

HALOGENOALKYL-, ALKENYL- AND ALKINYL-AZOLES

This is a continuation-in-part of application Ser. No. 885,046, filed July 14, 1986, now abandoned.

The present invention relates to new halogenoalkyl-, alkenyl- and alkinyl-azoles, several processes for the preparation thereof, and the use thereof in agents for combating pests.

It has already been disclosed that certain herbicides, such as, for example, 4-amino-6-tert.-butyl-3-methylthio-or -ethylthio-1,2,4-triazin-5-one; 1-amino-3-(2,2-dimethyl-propyl)-6-(ethylthio)-1,3,5-triazine-2,4-dione; 6-chloro-2-ethylamino-4-isopropylamino-1,3,5-triazine; 1-methoxy-1-methyl-3-(3,4-dichlorophenyl)-urea; 1,3-dimethyl-1-(benzo-1,3-thiazol-2-yl)-urea or 3-cyclohexyl-5,6-trimethyleneuracil, have photosynthesis-inhibiting properties (cf., for example, Carl Fedtke, Biochemistry and Physiology of Herbicide Action, Springer Verlag, 1982). However, it is a disadvantage in these herbicidal compounds that all weeds and weed grasses occurring are not always covered fully or that some species of crop plants are partially damaged at appropriately high application rates.

Synergistic mixtures of insecticidal active compounds, for example pyrethroids, with certain methylenedioxyphenyl derivatives, for example piperonyl butoxide, have likewise already been disclosed as synergists (cf., for example, K. Naumann, Chemie der Pflanzenschutz- und Schädlingsbekämpfungsmittel [The chemistry of plant-protection agents and pecticides] Springer-Verlag Berlin, volume 7 (1981) pages 3-6). However, the activity of these agents is not always completely satisfactory under the conditions which occur in practice.

New halogenoalkyl-, alkenyl- and alkinyl-azoles of the general formula (I)

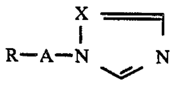

(I)

in which

X represents a nitrogen atom or a CH grouping,

R represents optionally substituted tert.-alkyl or optionally substituted cycloalkyl, and A represents one of the groupings —C≡C—,

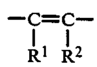 or 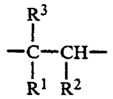

in which $R^1$ represents halogen, alkoxy or trialkylsilyloxy, $R^2$ represents hydrogen or halogen, and $R^3$ represents halogen, and their salts have now been found.

In the following, salts of compounds of the formula (I) are to be taken to mean the acid-addition salts and metal salt complexes.

It has furthermore been found that the halogenalkyl-, alkenyl- and alkinyl-azoles of the formula (I)

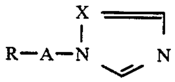

(I)

in which

X, R and A have the abovementioned meanings, and the salts thereof, are obtained when (a) in the case where X and R have the abovementioned meanings, and A represents the grouping

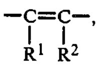

in which $R^1$ represents halogen, and $R^2$ represents hydrogen, azolyl ketones of the general formula (II)

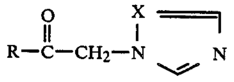

(II)

in which

X and R have the abovementioned meanings, are reacted with suitable halogenating agents in a fashion which is known per se, or (b) in the case where X and R have the abovementioned meanings and A represents the grouping

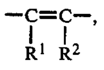

in which $R^1$ represents alkoxy or trialkylsilyloxy, and $R^2$ represents hydrogen, azolyl ketones of the general formula (II)

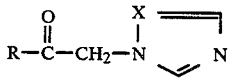

(II)

in which

X and R have the abovementioned meanings, are reacted with an alkylating agent or a silylating agent in a fashion which is known per se in the presence of a strong base and in the presence of a diluent, or (c) in the case where X and R have the abovementioned meanings and A represents the grouping —C≡C—, chlorovinylazole derivatives of the general formula (Ia)

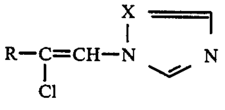

(Ia)

in which

X and R have the abovementioned meanings, are dehydrochlorinated by reacting with a strong base in the presence of a diluent, or (d) in the case where X and R have the abovementioned meanings and A represents the grouping

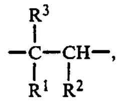

in which $R^1$, $R^2$ and $R^3$ have the abovementioned meanings, alkenyl-azoles of the general formula (Ib)

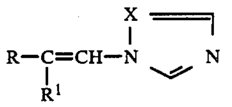
(Ib)

in which

X, R and $R^1$ have the abovementioned meanings, are reacted with halogen compounds of the formula (III)

$R^2$-$R^3$ (III)

in which $R^2$ and $R^3$ have the abovementioned meanings, in the presence of a diluent, or (e) in the case where X and R have the abovementioned meanings and A represents the grouping

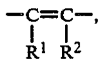

in which $R^1$ has the abovementioned meaning, and $R^2$ represents halogen, halogenalkyl-azoles of the formula (Ic)

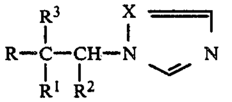
(Ic)

in which

X, R and $R^1$ have the abovementioned meanings, and $R^2$ and $R^3$ represents halogen, are dehydrohalogenated by reacting with a strong base in the presence of a diluent, and an acid or a metal salt is, if appropriate, added by conventional methods to the compounds of the formula (I) thus obtained.

The present invention furthermore relates to the use of compounds of the general formula (I), and the salts thereof, as synergists for combating pests, preferably vegetable pests and particularly preferably animal pests, and also synergistic mixtures of compounds of the formula (I), and the salts thereof, and known photosynthesis-inhibiting herbicides (for combating weeds) and, particularly preferably, synergistic mixtures of compounds of the formula (I), and the salts thereof, and known arthropodicides, in particular insecticides and acaricides (for combating arthropods), and the use of these mixtures for combating pests, preferably for combating arthropods.

The present invention also relates to the new herbicidal agents which contain known photosynthesis-inhibiting herbicides on the one hand and compounds of the formula (I), and the salts thereof, according to the invention as synergists on the other hand, and also to the use of these agents as herbicides.

The present invention furthermore relates, particularly preferably, to new pesticides which contain the compounds of the formula (I), and the salts thereof, as synergists besides arthropodicial, in particular insecticidal and acaricidal, active compounds, and to the use of these agents for combating pests.

Suitable arthropodicides (substances which are active against arthropods) are virtually all conventional active compounds (cf., for example, K.-H. Büchel, Pflanzenschutz und Schädlingsbekämpfungsmittel [Plant protection and pesticides], Thieme Verlag Stuttgart, 1977, and Farm Chemicals Handbook 1979, Meister Publishing Co, Willougby, 1979).

The compounds of the general formula (I), and the salts thereof, are preferably used together with arthropodical 1. carbamates and/or
2. carboxylates, including natural and synthetic pyrethroids, and/or
3. phosphorus compounds, such as phosphoric acid and phosphonic acid esters, including thiol and thiono compounds.

Although the new compounds of the general formula (I), and the salts thereof, have no inherent herbicidal action at conventional application rates, they do cause a considerable increase in the herbicidal action of photosynthesis-inhibiting active compounds—as has likewise been found. The synergistic effect found here is completely unexpected and surprising.

Since the newly found synergistic effect also concerns those weeds which are only inadequately damaged or even not covered by the photosynthesis-inhibiting active compounds used when applied alone at conventional application rates, the synergistic active compound combinations according to the invention represent a valuable enrichment of the art.

Surprisingly, the action of the active compound combinations, according to the invention, of compounds of the formula (I), and the salts thereof, and known arthropodicides against arthropods is also considerably greater than the action of these individual components or the sum of the actions of the individual components. It is furthermore considerably greater than the action of active compound combinations with the known commercially available synergist piperonyl butoxide. The compounds of the formula (I), and the salts thereof, which can be used according to the invention exhibit an excellent synergistic activity not only in the case of one active compound class, but in the case of active compounds from a very wide variety of chemical substance groups.

The synergistic action of the compounds of the general formula (I), and the salts thereof, is apparent, particularly preferably, in (1) carbamates of the formula (IV)

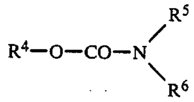

(IV)

in which $R^4$ represents an optionally substituted carbocyclic or heterocyclic aromatic radical or an optionally substituted oxime radical (the $R^4$ radicals mentioned further below being preferred), $R^5$ represents $C_1$–$C_4$-alkyl, and $R^6$ represents hydrogen, $C_1$–$C_4$-alkyl or a radical Y, where Y represents the —CO—$R^7$ radical, in which $R^7$ represents halogen, $C_1$–$C_4$-alkyl, $C_1$–$C_4$-alkoxy, $C_3$–$C_5$-alkenoxy, $C_3$–$C_5$-alkinoxy, $C_1$–$C_4$-alkylthio, $C_1$–$C_4$-alkylamino, di-$C_1$–$C_4$-alkylamino, $C_1$–$C_4$-alkylhydroxylamino, represents phenoxy, phenylthio or phenylene which is optionally substituted by halogen, nitro, cyano, trifluoromethyl, $C_1$–$C_4$-alkyl, $C_1$–$C_4$-alkoxy, $C_1$–$C_4$-alkylenedioxy, $C_1$–$C_4$-alkylthio or $C_1$–$C_4$-alkoxy-carbonyl, represents 2,3-dihydro-2,2-dimethyl-7-benzofuranyl, or represents the

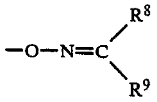

radical, in which $R^8$ represents hydrogen, $C_1$–$C_4$-alkyl or di-$C_1$–$C_4$-alkylaminocarbonyl, and $R^9$ represents $C_1$–$C_4$-alkyl, $C_1$–$C_4$-alkylthio, cyano-$C_1$–$C_4$-alkylthio or $C_1$–$C_4$-alkylthio-$C_1$–$C_4$-alkyl, or the two radicals $R^8$ and $R^9$ together represent $C_2$–$C_8$-alkanediyl which is optionally interrupted by oxygen, sulphur, SO or $SO_2$, or in which Y represents the —$S_o(O)_p$—$R^{10}$ radical, in which o represents 1 or 2, and p represents 0, 1 or 2, and $R^{10}$ represents optionally halogen-substituted $C_1$–$C_4$-alkyl, $C_3$–$C_5$-cycloalkyl, represents phenyl, benzyl or phenylethyl, each of which is optionally substituted by halogen, cyano, nitro, trifluoromethyl, trifluoromethoxy, trifluoromethylthio, $C_1$–$C_4$-alkyl or $C_1$–$C_4$-alkoxy, or represents the

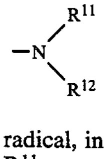

radical, in which $R^{11}$ represents $C_1$–$C_4$-alkyl, $C_3$–$C_5$-alkenyl, $C_3$–$C_5$-alkinyl, $C_3$–$C_6$-cycloalkyl or benzyl, and $R^{12}$ represents $C_1$–$C_4$-alkyl, $C_3$–$C_5$-alkenyl, $C_3$–C-alkinyl, $C_3$–$C_6$-cycloalkyl, benzyl, phenylethyl, halogenocarbonyl, formyl, $C_1$–$C_4$-alkyl-carbonyl, $C_1$–$C_4$-alkoxy-carbonyl, $C_1$–$C_4$-alkoxy-phenoxy-carbonyl, $C_3$–$C_5$-alkinoxy-carbonyl, $C_3$–$C_5$-alkenoxy-carbonyl, $C_1$–$C_4$-alkylthiocarbonyl, $C_1$–$C_4$-alkylamino-carbonyl, $C_1$–$C_4$-alkyl-hydroxylamino-carbonyl, $C_1$–$C_{10}$-alkyl-phenoxycarbonyl, di-$C_1$–$C_4$-alkyl-amino-carbonyl, phenylthiocarbonyl, phenoxy-carbonyl, 2,3-dihydro-2,2-dimethyl-7-benzofuranyloxy-carbonyl, represents phenylsulphenyl, phenylsulphinyl, phenylsulphonyl or phenyl, each of which is optionally substituted by halogen, cyano, nitro, trifluoromethyl, $C_1$–$C_{10}$-alkyl or $C_1$–$C_4$-alkoxy, or represents the

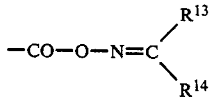

radical, in which $R^{13}$ has the meaning mentioned above for $R^8$, and $R^{14}$ has the meaning mentioned above for $R^9$, where, furthermore, the radicals $R^{11}$ and $R^{12}$ in the

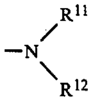

radicals, together, represent a hydrocarbon chain, having 3 to 8 carbon atoms, which is optionally interrupted by oxygen or sulphur, and in which, furthermore, $R^{10}$ can also represent the same radical to which the —$S_o(O)_p$—$R^{10}$ radical is bound.

Very particularly preferred active compound components are carbamates of the formula (IV), in which $R_4$ represents radicals from the series comprising phenyl, naphthyl, 2,3-dihydro-7-benzofuranyl, pyrazolyl or pyrimidinyl which are optionally substituted by $C_1$–$C_4$-alkyl, $C_2$–$C_4$-alkenyl, $C_1$–$C_4$-alkoxy, $C_1$–$C_4$-alkoxy-methyl, $C_1$–$C_4$-alkylthio, $C_1$–$C_4$-alkylthio-methyl, $C_1$–$C_4$-alkylamino, di-($C_1$–$C_4$-alkyl)-amino, di-($C_3$–$C_4$-alkenyl)-amino, halogen, dioxolanyl, methylenedioxy and/or by the —N=CH—$N(CH_3)_2$ radical, or in which $R^4$ represents an alkylideneamino radical of the formula

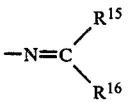

in which $R^{15}$ and $R^{16}$ have the meaning given above for $R^8$ and $R^9$ respectively, and $R^5$ represents $C_1$–$C_4$-alkyl, and $R^6$ represents hydrogen or $C_1$–$C_4$-alkyl (preferably hydrogen).

The following N-methylcarbamates may be mentioned as examples of the carbamates of the formula (IV): 2-methyl-phenyl, 2-ethyl-phenyl, 2-iso-propyl-phenyl, 2-sec-butyl-phenyl, 2-methoxy-phenyl, 2-ethoxy-phenyl, 2-iso-propoxy-phenyl, 4-methyl-phenyl, 4-ethyl-phenyl, 4-n-propyl-phenyl, 4-methoxy-phenyl, 4-ethoxy-phenyl, 4-n-propoxy-phenyl, 3,4,5-trimethyl-phenyl, 3,5-dimethyl-4-methylthio-phenyl, 3-methyl-4-dimethylaminophenyl, 2-ethylthiomethyl-phenyl, 1- naphthyl, 2,3-dihydro-2,2-dimethyl-7-benzofuranyl, 2,3-(dimethylmethylenedioxy)-phenyl, 2-(4,5-dimethyl-1,3-dioxolan-2-yl)-phenyl, 1-methylthio-ethylideneamino, 2-methylthio-2-methylpropylideneamino, 1-(2-cyanoethylthio)ethylideneamino and 1-methylthiomethyl-2,2-dimethylpropylideneamino N-methyl-carbamate.

The synergistic action of the compounds of the general formula (I) is furthermore preferably apparent in (2) carboxylates of the formula (V)

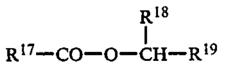

(V)

in which $R^{17}$ represents an open-chain or cyclic alkyl radical which is optionally substituted by halogen, alkyl, cycloalkyl, by alkenyl which is optionally substituted by halogen, alkyl and/or alkoxy, by phenyl or styryl which are optionally substituted by halogen or optionally halogen-substituted radicals from the series comprising alkyl, alkoxy, alkyldenedioxy and/or alkylthio, by spirocyclically linked, optionally halogen-substituted cycloalk(en)yl, which is optionally benzo-fused furthermore in which $R^{18}$ represents hydrogen, alkyl, halogenoalkyl, alkenyl, alkinyl or cyano, and $R^{19}$ represents an optionally substituted alkyl or aryl radical or a heterocyclic ring, or, together with $R^{18}$ and the carbon atom to which the two radicals are bound, forms a cyclopentenone ring.

Very particularly preferred active compound components are carboxylates of the formula (V)

in which $R^{17}$ (a) represents the

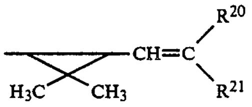

radical, in which $R^{20}$ represents hydrogen, methyl, fluorine, chlorine or bromine, and $R^{21}$ represents methyl, fluorine, chlorine, bromine, $C_1$–$C_2$-fluoroalkyl or $C_1$–$C_2$-chlorofluoroalkyl, or phenyl which is optionally substituted by halogen and/or optionally halogen-substituted radicals from the series comprising $C_1$–$C_4$-alkyl, $C_1$–$C_4$-alkoxy, $C_1$–$C_4$-alkylthio and/or $C_1$–$C_2$-alkylenedioxy, or in which both radicals $R^{20}$ and $R^{21}$ represent $C_2$–$C_5$-alkanediyl (alkylene); or in which $R^{17}$ (b) represents the

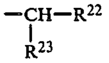

radical, in which $R^{22}$ represents phenyl which is optionally substituted by halogen and/or by optionally halogen-substituted radicals from the series comprising $C_1$–$C_4$-alkyl, $C_1$–$C_4$-alkoxy, $C_1$–$C_4$-alkylthio or $C_1$–$C_2$-alkylenedioxy, and $R^{23}$ represents isopropyl or cyclopropyl;

or in which $R^{17}$ (c) represents methyl or one of the radicals

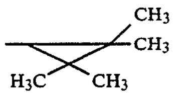

or

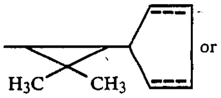

or

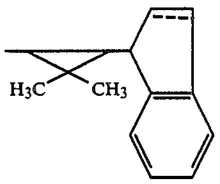

where the dotted lines are intended to indicate possible double bonds, and in which $R^{18}$ represents hydrogen, $C_1$–$C_4$-alkyl, $C_1$–$C_4$-halogenoalkyl cyano or ethinyl, and $R^{19}$ represents the radicals of the series comprising phenyl, furyl or tetrahydrophthalimido, where these radicals may be substituted by halogen and/or radicals from the series comprising $C_1$–$C_4$-alkyl, $C_2$–$C_4$-alkenyl, $C_1$–$C_4$-alkoxy, $C_2$–$C_4$-alkenoxy, $C_1$–$C_4$-alkylthio, $C_1$–$C_2$-alkylenedioxy, phenoxy and/or benzyl, which may themselves be substituted by halogen, and where $R^{19}$ preferably represents 2,3,5,6-tetrafluorophenyl or 4-methylthio-2,3,5,6-tetrafluorophenyl, 3,4-dichlorophenyl or tetrahydrophthalimido, or represents phenoxyphenyl which may be substituted in one or both phenyl rings by halogen.

Further particularly preferred carboxylates of the formula (V) are the naturally occurring pyrethroids (such as pyrethreum).

Examples of carboxylates of the formula (V) which may be mentioned are: 2,2,2-trichloro-1-(3,4-dichlorophenyl)-ethyl acetate, 3,4,5,6-tetrahydrophthalimidomethyl 2,2-dimethyl-3-(2-methyl-propen-1-yl)-cyclopropane-carboxylate, 3-phenoxy-benzyl 2,2-dimethyl-3-(2,2-dichloro-vinyl)cyclopropane-carboxylate, α-cyano-3-phenoxy-benzyl 2,2-dimethyl-3-(2,2-dichlorovinyl)-cycloprpane-carboxylate, α-cyano-4-fluoro-3-phenoxy-benzyl 2,2-dimethyl-3-(2,2-dichlorovinyl)-cyclopropanecarboxylate, 2,3,5,6-tetrafluorobenzyl 2,2-dimethyl-3-(2,2-dichlorovinyl)-cyclopropanecarboxylate, α-cyano-3-phenoxy-benzyl 2,2-dimethyl-3-(2,2-dibromovinyl)-cyclopropanecarboxylate and α-cyano-3-phenoxy-benzyl 3-methyl-2-(4-chloro-phenyl)-butanoate.

The synergistic action of the compounds of the general formula (I) is furthermore preferably apparent in (3) phosphoric acid esters and phosphonic acid esters of the general formula (VI)

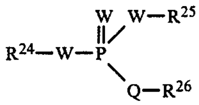

(VI)

in which

Q represents O, S, —NH— or a direct bond between the central P atom and $R^{26}$, and $R^{24}$ and $R^{25}$ are identical or different and represent optionally substituted alkyl or aryl, and $R^{26}$ represents hydrogen, optionally substituted alkyl, aryl, heteroaryl, aralkyl, alkenyl, dioxanyl or an oxime radical, or the same radical to which it is bound, and W is identical or different and represents O or S.

Particularly preferred phosphoric acid esters and phosphonic acid esters of the formula (VI) are those in which $R^{24}$ and $R^{25}$ are identical or different and represent $C_1$–$C_4$-alkyl or phenyl, $R^{26}$ represents hydrogen or alkyl, having 1 to 4 carbon atoms, which is optionally substituted by halogen, hydroxyl, cyano, optionally halogen-substituted phenyl, carbamoyl, alkylsulphonyl, alkylsulphinyl, alkylcarbonyl, alkoxy, alkylthio, alkoxy-carbonyl or alkylamino-carbonyl, the latter having up to 6 carbon atoms in each case, represents alkenyl, having up to 4 carbon atoms, which is optionally substituted by halogen, optionally halogen-substituted phenyl or $C_1$–$C_4$-alkoxycarbonyl, or represents the radical of the general formula

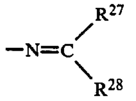

where $R^{27}$ and $R^{28}$ have the meaning given above for $R^8$ and $R^9$ respectively, or represent cyano or phenyl, and in which $R^{26}$ furthermore represents dioxanyl which is substituted by the same radical to which $R^{25}$ is bound, or $R^{26}$ represents the same radical to which it is bound, or $R^{26}$ represents phenyl which is optionally substituted by methyl, nitro, cyano, halogen and/or methylthio, where $R^{26}$, in addition, particularly preferably represents heteroaromatic radicals, such as pyridinyl, quinolinyl, quinoxalinyl, pyrimidinyl or benzo-1,2,4-triazinyl, which are optionally substituted by $C_1$–$C_4$-alkoxy, $C_1$–$C_4$-alkylthiomethyl, $C_1$–$C_4$-alkyl and/or by halogen.

The following may be mentioned individually: O,O-dimethyl or O,O-diethyl O-(2,2-dichloro- or 2,2-dibromovinyl) phosphate, O,O-diethyl O-(4-nitro-phenyl) thionophosphate, O,O-dimethyl O-(3-methyl-4-methylthiophenyl) thionophosphate, O,O-dimethyl O-(3-methyl-4-nitro-phenyl) thionophosphate, O-ethyl S-n-propyl O-(2,4-dichlorophenyl) thionophosphate, O-ethyl S-n-propyl O-(4-methylthio-phenyl) thionophosphate, O,O-dimethyl S-(4-oxo-1,2,3-benzotriazin-3-yl-methyl) thionothiolphosphate, O-methyl O-(2-iso-propyl-6-methoxypyrimidin-4-yl) thionomethanephosphonate, O,O-diethyl O-(2-iso-propyl-6-methyl-pyrimidin-4-yl) thionophosphate, O,O-diethyl O-(3-chloro-4-methyl-coumarin-7-yl) thionophosphate, O,O-dimethyl 2,2,2-trichloro-1-hydroxy-ethane-phosphonate and O,O-dimethyl S-(methylaminocarbonyl-methyl) thionophosphate.

In the general formulae, optionally substituted tert.-alkyl R denotes an alkyl group preferably having 4 to 12, in particular 4 to 8, carbon atoms, where at least one carbon atom must have bonds with 4 directly neighbouring carbon atoms and where this alkyl group may be substituted by one or more, preferably 1 to 3, in particular 1 or 2, identical or different substituents. Preferred substituents which may be mentioned are halogen atoms (fluorine, chlorine, bromine and/or iodine, preferably fluorine and/or chlorine). Preferred tert.-alkyl groups which may be mentioned are: $(CH_3)_3C-$, $Cl-CH_2-C(CH_3)_2-$, $F-CH_2C(CH_3)_2-$, $CH_3-C(C_2H_5)_2-$ and $(CH_3)_3C-CH_2-C(CH_3)_2-$.

Optionally substituted cycloalkyl R denotes cycloalkyl preferably having 3 to 7, in particular 3 to 6 and very particularly preferably 5 or 6, ring members (such as cyclopropyl, cyclobutyl, cyclopentyl, cyclohexyl and cycloheptyl), where the cycloalkyl radical may be substituted by one or more, preferably 1 to 3, in particular one, substituent. Substituents which may be mentioned are alkyl preferably having 1 to 4, in particular 1 or 2, carbon atoms, and halogen (fluorine, chlorine, bromine and iodine, preferably fluorine or chlorine). 1-Methyl-cyclopentyl and 1-methyl-cyclohexyl are particularly preferred.

In the definition of A, halogen $R^1$, $R^2$ and $R^3$ denote fluorine, chlorine, bromine and iodine, preferably fluorine, chlorine and bromine, in particular chlorine and bromine, and particularly preferably chlorine.

Alkoxy $R^1$ denotes alkoxy preferably having 1 to 6, in particular 1 to 4 and particularly preferably 1 or 2, carbon atoms.

The alkyl groups in the trialkylsilyloxy radical $R^1$ preferably contain 1 to 4, in particular 1 or 2, carbon atoms per alkyl group. The trimethylsilyloxyl radical is particularly preferred.

A particularly preferably represents the groups

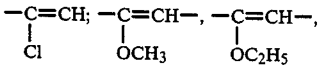

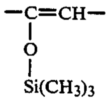 and $-CCl_2-CHCl-$.

X preferably denotes a nitrogen atom (which is part of a 1,2,4-triazol-1-yl ring).

Preferred salts of the (basic) compounds of the formula (I) which may be mentioned are the salts thereof wit hydrohalic acids, such as, for example, hydrochloric acid and hydrobromic acid, furthermore phosphoric acid, nitric acid, monofunctional and difunctional carboxylic acids and hydroxycarboxylic acids, such as, for example, acetic acid, maleic acid, succinic acid, fumaric acid, tartaric acid, citric acid, salicylic acid, sorbic acid and lactic acid, and also sulphonic acids, such as, for example, p-toluenesulphonic acid and 1,5-naphthalenedisulphonic acid.

The addition products of salts of metals of main groups II to IV and subgroups I and II and IV to VIII of the periodic system of the elements with the compounds of the formula (I) may furthermore be mentioned.

The compounds of the formula (I) preferably exist in free form (i.e. not as a salt).

In the preferred halogenoalkyl-, alkenyl- and alkinyl-azoles of the formula (I) according to the invention, X represents a nitrogen atom or a CH grouping, R represents optionally halogen-substituted tert.-alkyl having 4 to 8 carbon atoms, or cycloalkyl, having 3 to 6 carbon atoms, which is optionally substituted by alkyl having 1 to 4 carbon atoms and/or by halogen, and A represents the groupings $-C\equiv C-$,

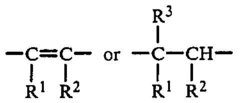

where $R^1$ represents halogen (preferably bromine or chlorine), alkoxy having 1 to 4 carbon atoms or trimethylsilyloxy, $R^2$ represents hydrogen or halogen (preferably bromine or chlorine) and $R^3$ represents halogen (preferably bromine or chlorine).

Particularly preferred compounds of the formula (I) are those in which

X represents a nitrogen atom or a CH grouping (preferably a nitrogen atom),

R represents tert.-alkyl, having 4 to 8 carbon atoms (preferably tert.-butyl) which is optionally substituted by chlorine and/or fluorine, or represents cyclopropyl, cyclopentyl or cyclohexyl which is optionally substituted by chlorine, methyl, ethyl and/or isopropyl, and A represents the grouping —C≡C— or A represents the grouping

in which (A)

$R^1$ represents chlorine, methoxy, ethoxy or trimethylsilyloxy, and $R^2$ represents hydrogen, or (b)

$R^1$ and $R^2$ represent chlorine, or

A represents the grouping

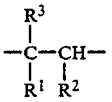

in which $R^1$, $R^2$ $R^3$ represent chlorine.

Very particularly preferred compounds of the formula (I) are those in which

X represents a nitrogen atom,

R represents the radicals $(CH_3)_3C$—, Cl—$CH_2C(CH_3)_2$— F—$CH_2C(CH_3)_2$—, $CH_3$—$C(C_2H_5)_2$— or $(CH_3)_3C$—$CH_2$—$C(CH_3)_2$—, and A represents the groupings —C≡C—, —CCl=CH—, —$C(OCH_3)$=CH—, —$C(OC_2H_5)$=CH—, —C$(OSi(CH_3)_3)$=CH— or —$CCl_2$—CHCl—.

If, for example, 3,3-dimethyl-1-(1,2,4-triazol-1-yl)-butan-2-one is used as starting material and phosphorus oxytrichloride and phosphorus pentachloride as halogenating agents, the course of process variant (a) according to the invention may be represented by the following equation:

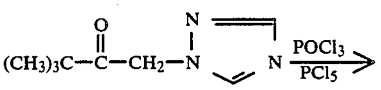

-continued

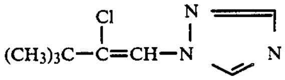

If, for example, 3,3-dimethyl-1-(1,2,4-triazol-1-yl)-butan-2-one is used as starting material, diethyl sulphate as alkylating agent and sodium hydride as strong base, the course of process variant (b) according to the invention may be represented by the following equation:

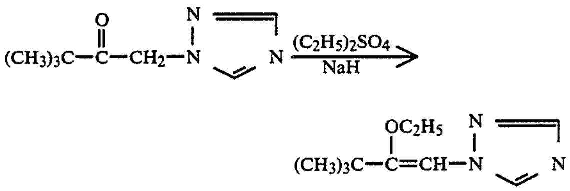

If, for example, 3,3-dimethyl-1-(1,2,4-triazol-1-yl)-2-chloro-but-1-ene is used as starting material and sodium ethylate as strong base, the course of process variant (c) according to the invention may be represented by the following equation:

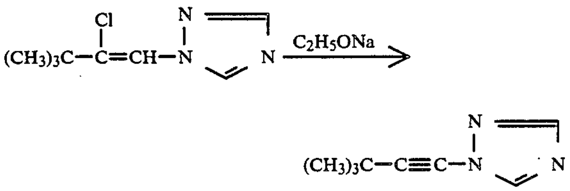

If, for example, 3,3-dimethyl-1-(1,2,4-triazol-1-yl)-2-chloro-but-1-ene and bromine are used as starting materials, the course of process varient (d) according to the invention may be represented by the following equation:

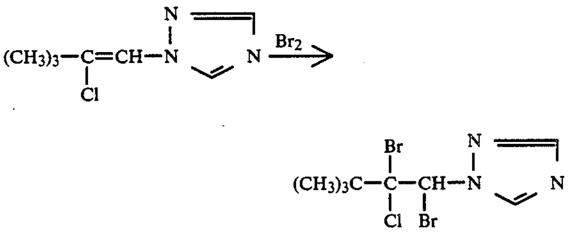

If, for example, 3,3-dimethyl-1-(1,2,4-triazol-1-yl)-1,2-dibromo-2-chloro-butane is used as starting material and sodium ethylate as strong base, the course of process variant (e) according to the invention may be represented by the following equation:

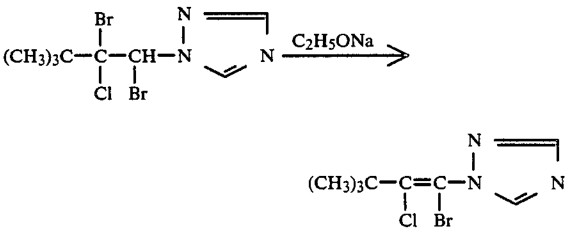

The azolyl ketones to be used as starting materials for carrying out process variants (a) and (b) according to the invention are known (cf., for example, DE-OS (German Published Specification) No. 2,431,407, EP No. 0,031,911, EP No. 0,054,865, DE-OS (German Published Specification No. 2,610,022, DE-OS (German Published Specification) No. 2,638,470, DE-OS (German Published Specification) No. 2,820,361, DE-OS (German Published Specification) No. 3,145,857 and DE-OS (German Published Specification) No. 3,145,858); or they can be prepared by processes which are known in principle, such as by reacting the appropriate halogenomethyl ketones with the appropriate azole in the presence of an inert organic solvent, such as, for example, acetone or acetonitrile, and in the presence of an acid-binding agent, such as, for example, potassium carbonate or triethylamine, at temperatures between 20° C. and 150° C.

The chlorovinyl-azole derivatives of the formula (Ia) to be used as starting materials for carrying out process variant (c) according to the invention are new compounds and can be prepared according to process variants (a) and (b) according to the invention. They are part of the present invention.

The alkenyl-azoles of the formula (Ib) to be used as starting materials for carrying out process variant (d) according to the invention are likewise new compounds and can be prepared according to process variants (a) and (b) according to the invention. They are likewise part of the present invention.

The halogenoalkyl-azoles of the formula (Ic) to be used as starting materials for carrying out process variant (e) according to the invention are likewise new compounds and can be prepared according to process (d) according to the invention. These compounds are likewise part of the present invention.

Suitable halogenating agents for process variant (a) according to the invention are all halogenating agents which can conventionally be used for converting aliphatic ketones into corresponding vinyl halides, in particular phosphorus pentahalides, such as, for example, phosphorus pentachloride and phosphorus pentabromide, and also phosphorus oxytrihalides, such as, for example, phsophorus oxytrichloride and phosphorus tribromide.

Process variant (a) according to the invention is preferably carried out without diluent.

The reaction temperatures can be varied within a relatively wide range when carrying out process variant (a) according to the invention. In general, the process is carried out at temperatures between 20° C. and 200° C., preferably at temperatures between 40° C. and 180° C.

When carrying out process variant (a) according to the invention, 1 to 2 moles of the halogenating agent are preferably employed per mole of the azolyl ketone of the formula (II).

The halogenovinyl-azole derivatives of the formula (Ib)

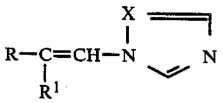

(Ib)

in which

R and X have the abovementioned meanings, and $R^1$ represents halogen, such as chlorine or bromine, can also be obtained by reacting the azolyl ketones of the formula (II) with triphenyl phosphine and a hexahalogenoethane, such as hexachloroethane or hexabromoethane, in the temperature range 60° C. to 200° C., preferably in the temperature range 80° C. to 180° C., without diluent (in this respect, cf. also the preparation examples).

The alkylating agents and silylating agents used for process variant (b) according to the invention are, in particular, dialkyl sulphates, such as, for example, dimethyl sulphate and diethyl sulphate, or trialkylsilyl halides, such as, for example, trimethylsilyl chloride.

Suitable strong bases for carrying out process variant (b) according to the invention are all conventional strong inorganic and organic bases. These preferably include alkali metal hydrides and alkali metal amides, such as sodium hydride and amide and potassium hydride and amide; tertiary alkylamines, such as triethylamine; alkali metal alcoholates, such as sodium methylate, sodium ethylate and potassium tert.-butylate; and also alkali metal hydroxides, such as sodium hydroxide and potassium hydroxide.

Possible diluents for carrying out process variant (b) according to the invention are all conventional inert organic solvents. Particularly suitable are ethers, such as dioxane and tetrahydrofuran; formamides, such as dimethylformamide; and sulphoxides, such as dimethyl sulphoxide.

The reaction temperatures can be varied within a relatively wide range when carrying out process variant (b) according to the invention. In general, the process is carried out at temperatures between 20° C. and 100° C., preferably between 40° C. and 80° C.

When carrying out process variant (b) according to the invention, 1 mole of the alkylating agent is preferably employed per mole of the azolyl ketone of the formula (II).

For process variant (c) according to the invention, suitable strong bases are all conventional strong inorganic and organic bases. These preferably include alkali metal hydrides and alkali metal amides, such as sodium hydride and amide and potassium hydride and amide; tertiary alkylamines, such as triethylamine; alkali metal alcoholates, such as sodium methylate, sodium ethylate and potassium tert.-butylate; and alkali metal hydroxides, such as sodium hydroxide and potassium hydroxide.

Possible diluents for carrying out process variant (c) according to the invention are all conventional inert organic solvents. Ethers, such as dioxane and tetrahydrofuran; formamides, such as dimethylformamide; sulphoxides, such as dimethyl sulphoxide, and alcohols, such as ethanol, are also particularly suitable here.

The reaction temperatures can be varied within a relatively wide range when carrying out process variant (c) according to the invention. In general, the process is carried out at temperatures between 0° C. and 120° C., preferably between 20° C. and 100° C.

When carrying out process variant (c) according to the invention, 1 to 2 moles of base are preferably employed per mole of the chlorovinyl-azole derivative of the formula (Ia).

Process variant (d) according to the invention is carried out using halogen compounds of the formula (III). In the formula (III), $R^2$ and $R^3$ preferably represent chlorine and/or bromine, in particular chlorine. Examples of halogen compounds of the formula (III) which may be mentioned are chlorine ($Cl_2$), bromine ($Br_2$) and "bromine chloride" (BrCl)—the latter generated, if appropriate, in situ from bromine and chlorine.

Possible diluents for carrying out process variant (d) according to the invention are all conventional inert organic solvents. Particularly suitable are halogenated hydrocarbons, such as, for example, methylene chloride, 1,2-dichloroethane, chloroform, tetrachloromethane, chlorobenzene and dichlorobenzenes.

The reaction temperatures can be varied within a relatively wide range in process variant (d) according to the invention. In general, the process is carried out at temperatures between 0° C. and 200° C., preferably at temperatures between 20° C. and 150° C.

When carrying out process variant (d) according to the invention, 1 to 3 moles of a halogen compound of the formula (III) are preferably employed per mole of alkenyl-azole of the formula (Ib).

For process variant (e) according to the invention, suitable strong bases are all conventional strong inorganic and organic bases. These preferably include alkali metal hydrides and alkali metal amides, such as sodium hydride and amide and potassium hydride and amide; tertiary alkylamines, such as triethylamine; alkali metal alcoholates, such as sodium methylate, sodium ethylate and potassium tert.-butylate; and alkali metal hydroxides, such as sodium hydroxide and potassium hydroxide.

Possible diluents for carrying out process variant (e) according to the invention are all conventional inert organic solvents. Ethers, such as dioxane and tetrahydrofuran; formamides, such as dimethylformamide; sulphoxides, such as dimethyl sulphoxide, and alcohols, such as ethanol, are also particularly suitable here.

The reaction temperatures can be varied within a relatively wide range when carrying out process variant (e) according to the invention. In general, the process is carried out at temperatures between 0° C. and 120° C., preferably between 20° C. and 100° C.

When carrying out process variant (e) according to the invention, 1 to 2 moles of base are preferably employed per mole of the halogenoalkyl-azole of the formula (Ic).

Suitable acids for the preparation of acid-addition salts of the compounds of the general formula (I) are preferably those which have already been mentioned as preferred acids in connection with the description of the acid-addition salts according to the invention.

Acid-addition salts of the compounds of the formula (I) can be obtained in a simple fashion according to conventional salt-formation methods, for example by dissolving a compound of the general formula (I) in a suitable inert solvent and adding the acid, for example hydrochloric acid, and can be isolated in the known fashion, for example by filtering off, and, if necessary, purified by washing with an inert organic solvent.

Suitable metal salts for the preparation of metal salt complexes of the compounds of the general formula (I) are preferably those which have already been described further above.

The metal salt complexes of compounds of the general formula (I) can be obtained in a simple fashion by conventional processes, i.e., for example, by dissolving the metal salt in alcohol, for example ethanol, and adding to a solution of compounds of the general formula (I). Metal salt complexes can be isolated in a known fashion, for example by filtering off, and, if necessary, purified by recrystallization.

Photosynthesis-inhibiting herbicide active compounds for the active compound combinations already mentioned above which may preferably be mentioned are the following compounds of the general formula (VII-A) to (VII-J):

(A) Triazinone derivatives of the formula

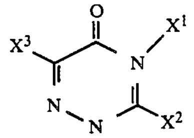

(VII-A)

in which $X^1$ represents amino, optionally substituted alkylideneamino or alkyl having 1 to 2 carbon atoms;

$X^2$ represents alkylthio having 1 to 2 carbon atoms, alkyl- and dialkylamino in each case having 1 to 2 carbom atons in each alkyl part, or alkyl having 1 to 4 carbon atoms; and $X^3$ represents optionally halogen-substituted tert.-butyl or optionally substituted phenyl.

(B) Triazinedione derivatives of the formula

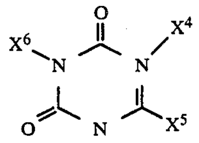

(VII-B)

in which $X^4$ represents amino, optionally substituted alkylideneamino or alkyl having 1 to 2 carbon atoms, $X^5$ represents alkylthio having 1 to 2 carbon atoms, alkyl- and dialkylamino in each case having 1 to 2 carbon atoms in each alkyl part, or alkyl having 1 to 4 carbon atoms; and $X^6$ represents alkyl having 1 to 6 carbon atoms or optionally substituted phenyl.

(C) Triazine derivatives of the formula

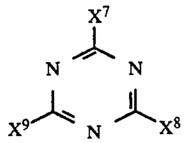

(VII-C)

in which $X^7$ represents chlorine, alkoxy or alkylthio, in each case having 1 to 2 carbon atoms, $X^8$ represents alkylamino having 1 to 4 carbon atoms in the alkyl part; and $X^9$ represents optionally cyano-substituted alkyl having 1 to 4 carbon atoms.

(D) Urea derivatives of the formula

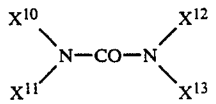

(VII-D)

in which $X^{10}$ represents optionally substituted phenyl, benzothiazolyl or optionally substituted thiadiazolyl;

$X^{11}$ represents hydrogen or methyl;

$X^{12}$ represents methyl; and $X^{13}$ represents hydrogen, alkyl having 1 to 4 carbon atoms, alkoxy having 1 to 2 carbon atoms, or alkinyl having 2 to 4 carbon atoms.

(E) Carboxanilide derivatives of the formula $X^{14}$—CO—NH—$X^{15}$ (VII-E)

in which $X^{14}$ represents alkyl having up to 6 carbon atoms, alkoxy, having 1 to 4 carbon atoms, alkenyl having 2 to 4 carbon atoms, or cycloalkyl having 3 to 6 carbon atoms; and $X^{15}$ represents optionally substituted phenyl.

(F) Uracil derivatives of the formula

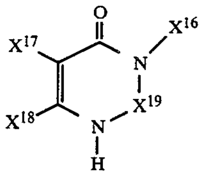

(VII-F)

in which $X^{16}$ represents alkyl having 1 to 6 carbon atoms, or cycloalkyl having 5 to 7 carbon atoms;

$X^{17}$ represents halogen;

$X^{18}$ represents alkyl having 1 to 2 carbon atoms, or $X^{17}$ and $X^{18}$ together represent an optionally substituted alkylene chain or an optionally substituted fused benzene ring; and $X^{19}$ represents the CO or $SO_2$ group.

(G) Biscarbamate derivatives of the formula

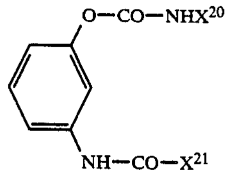

(VII-G)

in which $X^{20}$ represents alkyl having 1 to 4 carbon atoms, or optionally substituted phenyl; and $X^{21}$ represents alkoxy having 1 to 4 carbon atoms, or dialkylamino having 1 to 2 carbon atoms in each alkyl part.

(H) Pyridazinone derivatives of the formula

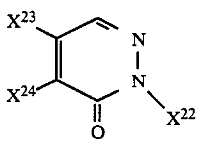

(VII-H)

in which $X^{22}$ represents optionally substituted phenyl;

$X^{23}$ represents amino, alkylamino or dialkylamino in each case having 1 to 2 carbon atoms in each alkyl part; and $X^{24}$ represents halogen.

(J) Hydroxybenzonitrile derivatives of the formula

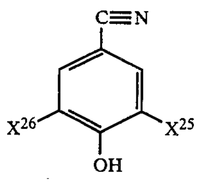

(VII-J)

in which $X^{25}$ represents halogen; and $X^{26}$ represents halogen.

Particularly preferred photosynthesis-inhibiting active compounds of the general formulae (VII-A) to (VII-J) are the following:

(A) Triazinone derivatives of the formulae

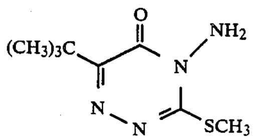

(VII-A-1)

(metribuzin)

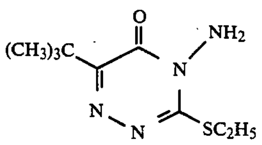

(VII-A-2)

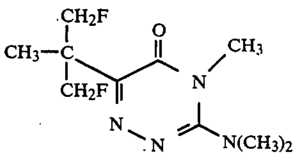

(VII-A-3)

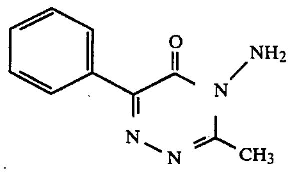

(VII-A-4)

(metamitron)

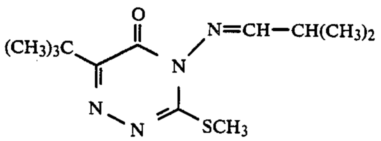

(VII-A-5)

(isomethiozin)

(B) Triazinedione derivative of the formula

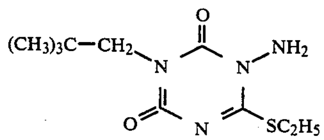

(VII-B-1)

(ametridione)

(C) Triazine derivatives of the formulae (VII-C-1)
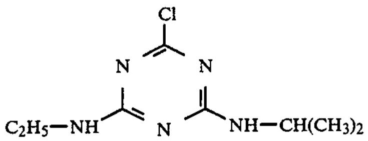
(atrazine)
(VII-C-2)
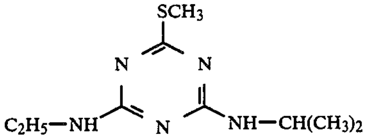
(atmetryn)
(VII-C-3)
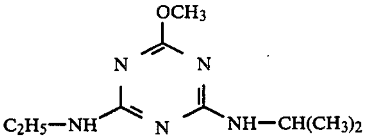
(atraton)
(VII-C-4)
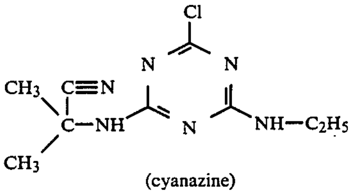
(cyanazine)
(VII-C-5)
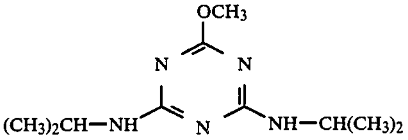
(prometon)
(VII-C-6)
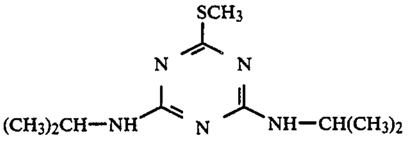
(prometryn)
(VII-C-7)
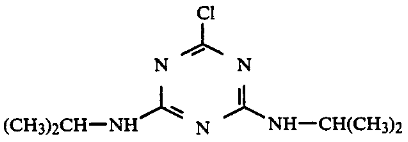
(propazine)
(VII-C-8)
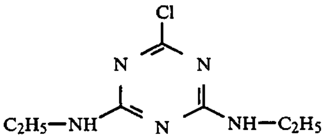
(simazine)
(VII-C-9)
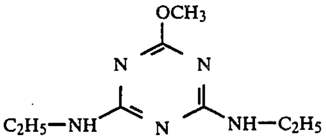
(simeton)
-continued
(VII-C-10)
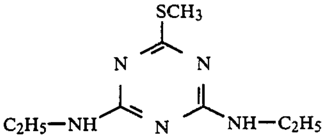
(simetryn)
(VII-C-11)
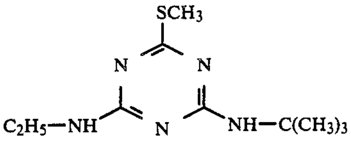
(terbutryn)
(VII-C-12)
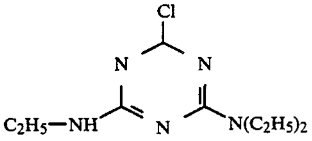
(trietazine)
(D) Urea derivatives of the formulae
(VII-D-1)
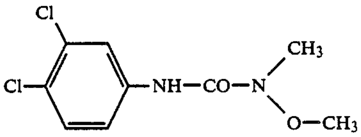
(linuron)
(VII-D-2)
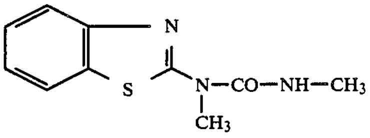
(methabenzthiazuron)
(VII-D-3)
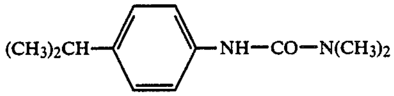
(isoproturon)
(VII-D-4)
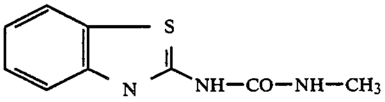
(benzthiazuron)
(VII-D-5)
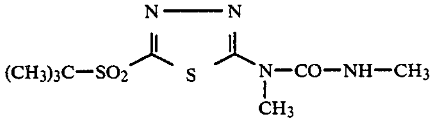
(buthiuron)
(VII-D-6)
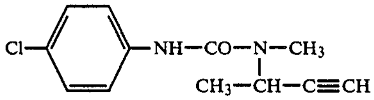
(buturon)

-continued (VII-D-7)

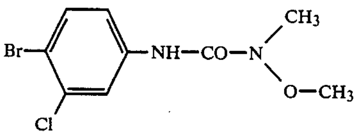

(chlorbromuron)

(VII-D-8)

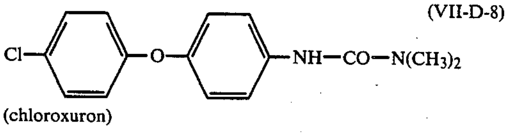

(chloroxuron)

(VII-D-9)

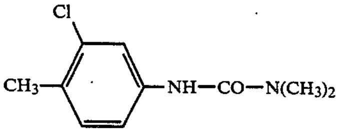

(chlortoluron)

(VII-D-10)

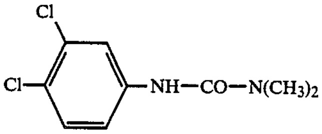

(diuron)

(VII-D-11)

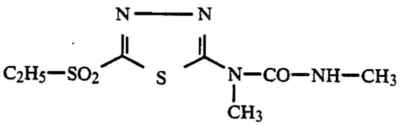

(ethidimuron)

(VII-D-12)

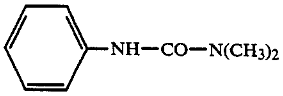

(fenuron)

(VII-D-13)

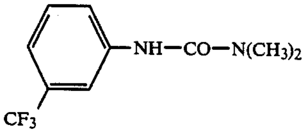

(fluometuron)

(VII-D-14)

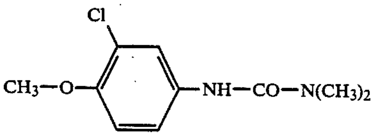

(metoxuron)

(VII-D-15)

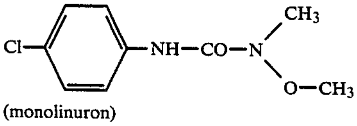

(monolinuron)

(VII-D-16)

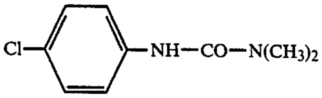

(monuron)

-continued (VII-D-17)

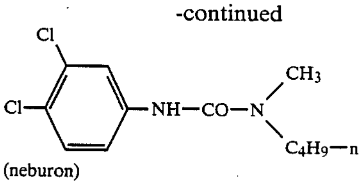

(neburon)

(VII-D-18)

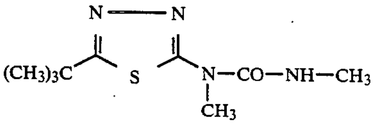

(tebuthiuron)

(VII-D-19)

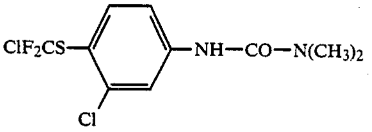

(thiochlormethyl)

(E) Carboxanilide derivatives of the formulae (VII-E-1)

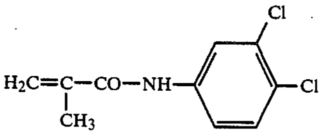

(chloranocryl)

(VII-E-2)

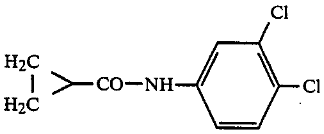

(cypromid)

(VII-E-3)

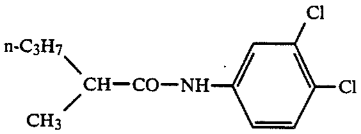

(Karsil)

(VII-E-4)

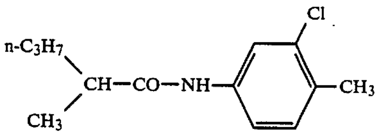

(pentanochlor)

(VII-E-5)

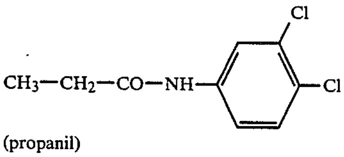

(propanil)

(VII-E-6)

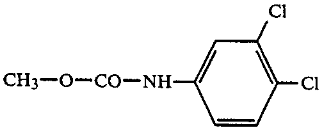

(Swep)

(F) Uracil derivatives of the formulae (VII-F-1)

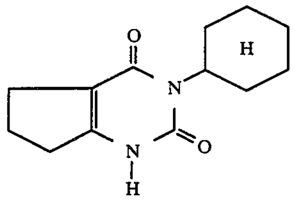

(lenacil)

(VII-F-2)

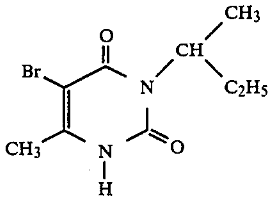

(bromacil)

(VII-F-3)

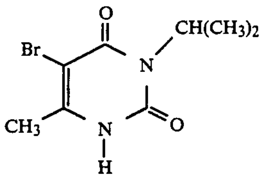

(isocil)

(VII-F-4)

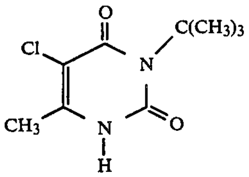

(terbacil)

(VII-F-5)

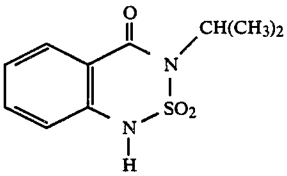

(bentazon)

(G) Biscarbamate derivatives of the formulae (VII-G-1)

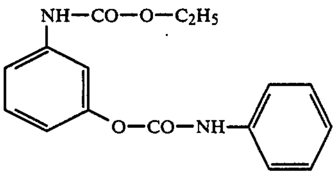

(desmedipham)

(VII-G-2)

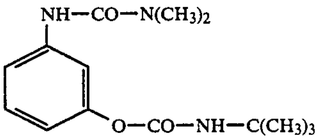

(karbutilate)

-continued (VII-G-3)

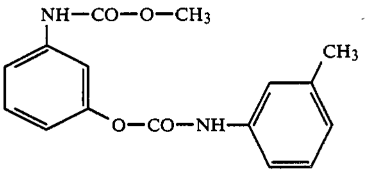

(phenmedipham)

(H) Pyridazinone derivatives of the formulae (VII-H-1)

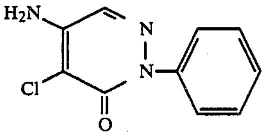

(pyrazon)

(VII-H-2)

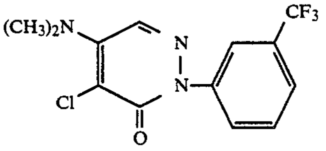

(metflurazon)

(VII-H-3)

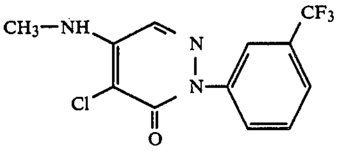

(norflurazon)

(J) Hydroxybenzonitrile derivatives of the formulae (VII-J-1)

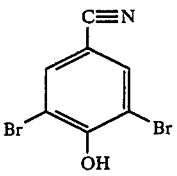

(bromoxynil)

(VII-J-2)

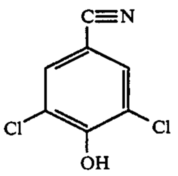

(chloroxynil)

(VII-J-3)

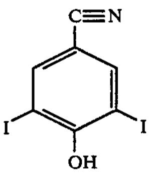

(ioxynil)

The photosynthesis-inhibiting active compounds of the formulae (VII-A) to (VII-J) are known (cf., for example, Carl Fedtke, Biochemistry and Physiology of Herbicide Action, Springer-Verlag, 1982).

The weight ratios of the active compounds in the new active compound combinations can vary within a relatively broad range. In general, 0.25 to 100, preferably 5 to 50, in particular 10 to 20, parts by weight of the compound of the formula (I) (synergist) are present per part by weight of the photosynthesis-inhibiting active compound (herbicidal active compound).

The photosynthesis-inhibiting active compounds have strong herbicidal actions. Nevertheless, they have an action against some weeds, such as, for example, *Galium aparine, Iopmoea hederacea, Datura stramonium, Cirsium arvense, Convoluvulus arvensis* or *Solanum nigrum*, and some weed grasses, such as, for example, *Agropyron repens, Avena fatua, Cynodon dactylon,* Cyperus ssp. and *Lolium rigidum*, which is not always adequate. The active compound combinations according to the invention extend the range of action of the compounds of the formulae (VII-A) to (VII-J) and thereby permit combating of these weeds which can only be combated with difficulty or not at all by the herbicidal active compounds alone.

The active compound combinations, according to the invention, of photosynthesis-inhibiting herbicides and compounds of the formula (I) can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portuluca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Vicia, Nicotiana, Lycopersicon, Arachis, Brassica, Lactuca, Cucumis and Cuburbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compound combinations according to the invention is in no way restricted to these genera, but also extends in the same manner to other plants.

In particular, besides a good action against grass-like (monocotyledon) weeds, the active compound combinations according to the invention exhibit a good herbicidal action in the case of dicotyledon weeds.

The new active compound combinations for combating weeds can be used for combating weeds as such or in their formulations, also mixed with other known herbicides, ready-to-use formulations or tank mixes again being possible. Mixtures with other known active compounds, such as fungicides, insecticides, acaricides, nematicides, bird repellents, phytohormones, plant nutrients and agents which improve soil structure are also possible.

The new active compound combinations can be used as such, in the form of their formulations or in their use forms prepared therefrom by further dilution, such as ready-to-use solutions, suspensions, emulsions, powders, pastes and granules. They are used in the customary manner, for example by watering, spraying, atomizing or scattering.

The active compound combinations, according to the invention, for combating weeds can be applied, together or in separate applications, either before or after sowing or after emergence of the plants. The sequence of application is unimportant during application.

When using the synergists according to the invention, the conventional application rate of the herbicide of the formulae (VII-A) to (VII-J) can be reduced. In the case of soil surface treatment, the application rate of a herbicidal photosynthesis-inhibiting active compound is between 0.01 and 3.0 kg/ha, preferably between 0.05 and 2.0 kg/ha. In the case of soil surface treatment, the application rate of synergistic compounds of the formula (I) is between 0.1 and 10 kg/ha, preferably between 0.5 and 3 kg/ha.

The good herbicidal action of the active compound combinations according to the invention can be seen from use example (A). Whereas the herbicidal action of the individual active compounds has weaknesses, the combinations exhibit a weed action which extends beyond a simple action summation.

In herbicides, a synergistic effect is always present when the herbicidal action of the active compound combination is greater than the sum of the actions of the individual active compounds applied.

The active compound combinations, according to the invention, of arthropodicides and compounds of the formula (I), and the salts thereof, and the arthropodicidal pesticides which contain these active compound combinations exhibit not only a rapid knock-down action, but also cause the destruction of the animal pests, preferably arthropods, in particular insects and arachnida (including midges) encountered in agriculture (including animal husbandry), in forestry, in the protection of stored products and materials, and in the household and hygiene field. They are active against normally sensitive and resistant species and against all or some stages of development.

The animal pests which can be combated using the compounds of the formula (I), and the salts thereof, include, for example:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and *Scutigera spec.* From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Perpiplaneta americana, Leucophaea maderae, Blattella germanica, Acheta domesticus, Gryllotalpa spp., Locusta migratoria migratorioides, Melanoplus differentialis* and *Schistocerca gregaria.* From the order of the Dermaptera, for example, *Forficula auricularia.* From the order of the Isoptera, for example, Reticulitermes spp. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesma quad-*

*rata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma Lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocollectis blancardella, Hyponomeuta padella, Plutella maculipennis, Malacosoma neustria, Euproctis chrysorrhoea,* Lymantria spp. *Bucculatrix thurberiella, Phyllocnistic citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*. From the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varive stis,* Atomaria spp., *Oryzaephilus surinamensis,* Antho nomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallonsolstitialis* and *Costelytra zealandica*. From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa*. From the order of the Siphonaptera, for example, *Xenopsylla cheopis* and Ceratophyllus spp. From the order of the Arachnida, for example, *Scorpio maurus* and *Latrodectus mactans*. From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chlorioptes spp., Sarcoptes spp., Tarsonemus spp., *Bryobia praetiosa,* Panonychus spp. and Tetranychus spp.

Depending on their particular physical and/or chemical properties, the active compound combinations of the compounds of the formula (I), and the salts thereof, and the other active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant those liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compound combinations according to the invention are applied in the form of their commercially available formulations and/or the use forms prepared from these formulations.

The total content of active compound (including synergist) in the use forms prepared from commercially available formulations can vary within broad limits. The active compound concentration in the use forms can be from 0.001 to 95% by weight of active compound combination, preferably between 0.01 and 10% by weight.

Application takes place in a customary manner appropriate for the use forms.

When used against hygiene pests and pests of stored products, the active compound combinations for combating arthropods are distinguished by an excellent residual action on wood and clay as well as good stability to alkali on limed substrates.

The weight ratios of the synergists of the general formula (I), or the salts thereof, and active compounds (arthropodicides or herbicides) can be varied within a relatively broad range. In general, the compounds of the formula (I), or the salts thereof, used as synergists are employed with the other active compounds in mixing ratios between 1:100 and 100:1, preferably between 1:20 and 20:1, in particular between 1:10 and 10:1 (parts by weight).

The good arthropodicidal action of the active compound combinations, according to the invention, of compounds of the formula (I), or the salts thereof, and arthropodioides can be seen from use examples (B) and (C).

The preparation process according to the invention is illustrated with reference to the following preparation examples:

EXAMPLE 1

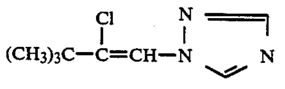

Process Variant a 93.0 g (0.45 mole) of phosphorus pentachloride are added, with stirring, to a solution of 50 g (0.29 mole) of 3,3-dimethyl-1-(1,2,4-triazol-1-yl)-butan-2- one in 100 ml of phosphorus oxytrichloride. The reaction mixture is warmed at 100° C. for 2 hours, subsequently poured onto ice, adjusted to pH 8 using concentrated sodium hydroxide solution, and extracted with dichloromethane. After removing the dichloromethane in a rotary evaporator, the residue is distilled.

42 g (76% of theory) of 2-chloro-3,3-dimethyl-1-(1,2,4-triazol-1-yl)-but-1-ene of boiling point 77° C./0.08 mbar are obtained.

Additional process variant:

396 g (1.7 moles) of hexachloroethane and (437 g (1.7 moles) of triphenyl phosphine are slowly warmed together with 284 g (1.7 moles) of 3,3-dimethyl-1-(1,2,4-triazol-1-yl)-butan-2-one. An exothermic reaction commences at an internal temperature of 70° C., the temperature increasing to 115° C. The reaction mxiture is heated to 170° C. on an oil bath and stirred at 170° C. for 6 hours. After cooling, the dark product is dissovled in 1.5 liters of dichloromethane, and 2 liters of water are added. The mixture is adjusted to pH 6-7 using potassium carbonate, with stirring, and the organic phase is separated off and concentrated in a rotary evaporator. The residue is extracted with hot petroleum ether (3 times 1 liter), and the extract is evaporated. The remaining oil is distilled.

221 g (70% of theory) of 2-chloro-3,3-dimethyl-1-(1,2,4-triazol-1-yl)-but-1-ene of boiling point 85° C./0.12 mbar are obtained.

EXAMPLE 2

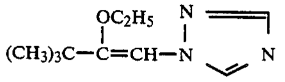

Process Variant b 9 g (0.3 mole) of 80 per cent strength sodium hydride are carefully added to a solution of 50 g (0.29 mole) of 3,3-dimethyl-1-(1,2,4-triazol-1-yl)-butan-2-one in 200 ml of dimethylformamide. After stirring for 10 minutes, 46.2 g (0.3 mole) of diethyl sulphate are added dropwise at 30°-40° C., and the reaction mixture is stirred at 60° C. for 2 hours; the mixture is subsequently poured into water. The product is extracted with dichloromethane, the solvent is removed in a rotary evaporator, and the residue is distilled via a Vigreux column.

16 g (28% of theory) of 2-ethoxy-3,3-dimethyl-1-(1,2,4-triazol-1-yl)-but-1-ene of boiling point 85°-90° C./0.665 mbar are obtained.

EXAMPLE 3

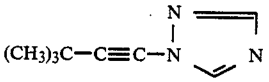

Process Variant c 18.6 g (0.1 mole) of 3,3-dimethyl-1-(1,2,4-triazol-1-yl)-2-chloro-but-1-ene are added to a solution of 3 g (0.13 mole) of sodium in 100 ml of ethanol at 20° C., and the mixture is refluxed for 1 hour. The excess ethanol is subsequently removed in a rotary evaporator, the residue is poured into water, and the product is extracted with dichloromethane. After removing the solvent, the oil remaining is distilled.

11 g (74% of theory) of 3,3-dimethyl-1-(1,2,4-triazol-1-yl)-but-1-ine of boiling point 150° C./0.266 mbar are obtained.

EXAMPLE 4

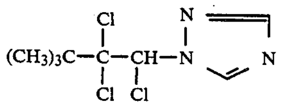

Process Variant d

Within about 45 minutes, 42 g (0.6 mole) of chlorine are passed into a boiling solution of 55.7 g (0.3 mole) of 2-chloro-3,3-dimethyl-1-(1,2,4-triazol-1-yl)-butene and 200 ml of chlorobenzene. After cooling, the precipitated solid is filtered off and the filtrate is concentrated in a rotary evaporator. The oily residue remaining is distilled under reduced pressure.

49.6 g (64% of theory) of 3,3-dimethyl-1-(1,2,4-triazol-1-yl)-1,2,2-trichloro-butane of boiling point 88° C. to 94° C./0.1 mbar are obtained.

EXAMPLE 5

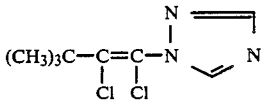

Process Variant e 1.3 g (0.055 mole) of sodium are added to 80 ml of ethanol. 12.8 g (0.05 mole) of 3,3-dimethyl-1-(1,2,4-triazole-1-yl)-1,2,2-trichloro-butane are then added to this mixture, and the reaction mixture is stirred at 50° C. for about 15 hours. After concentrating in a rotary evaporator, the residue is distributed between methylene chloride and water, and the organic phase is separated off. After drying using sodium sulphate, the mixture is filtered, the filtrate is concentrated, and the residue is distilled under reduced pressure.

7.1 g (65% of theory) of 1,2-dichloro-3,3-dimethyl-1-(1,2,4-triazol-1-yl)-butene of boiling point 87° C. to 93° C./0.4 mbar are obtained.

The following compounds of the general formula

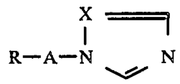

(I)

are obtained in analogous fashion and corresponding to the process variants according to the invention:

| Example No. | R | A | X | Boiling point (°C./mbar) |
|---|---|---|---|---|
| 6 | $(CH_3)_3C-$ | 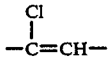 | $-CH-$ | 88/0.2 |
| 7 | $(CH_3)_3C-$ | 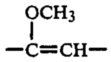 | N | 74/0.133 |
| 8 | 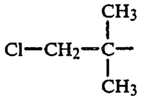 | 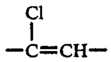 | N | 130/0.266 |
| 9 | 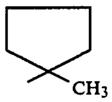 | 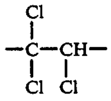 | N | [m.p. 95° C.] |
| 10 | 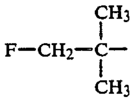 | 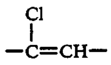 | N | 75/0.8 |
| 11 | $(CH_3)_3C-$ | 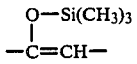 | N | 80/0.266 |
| 12 | 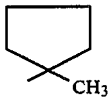 | 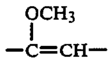 | N | 125/0.532 |
| 13 | 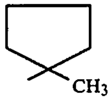 | 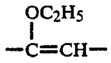 | N | 126/0.266 |
| 14 | 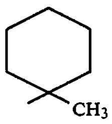 | 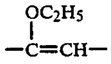 | N | 128/0.2 |
| 15 | 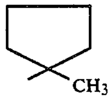 | 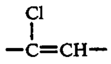 | N | 103/0.133 |
| 16 | 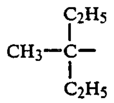 | 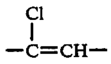 | N | 84/0.133 |

-continued

| Example No. | R | A | X | Boiling point (°C./mbar) |
|---|---|---|---|---|
| 17 | 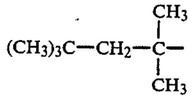 | 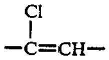 | N | 100/0.133 |

USE EXAMPLE A (herbicide synergism)

Pre-emergence test

Solvent: 5 parts by weight of acetone

Emulsifier: 1 part by weight of alkylaryl polyglycol ether

To produce a suitable preparation of active compound, 1 part by weight of herbicidal active compound or synergist or a mixture of herbicidal active compound and synergist is mixed with the stated amount of solvent, the stated amount of emulsifier is added and the concentrate is diluted with water to the desired concentration.

Seeds of thê test plants are sown in normal soil and, after 24 hours, watered with the preparation of the herbicide of the prepartion of the synergist or with the preparation of the synergist and the herbicidal active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)

100%=total destruction

The active compounds, application rates and results can be seen from Table A below.

TABLE A

Pre-emergence test
Synergistic action of compounds of the formula (I) (= synergist S) and 4-amino-6-tert.-butyl-3-methyl-thio-1,24-triazin-5-one (VII-A-1) (= herbicide H) on *Ipomoea hederacea*. Th application rate in kg/ha refers to the content of active compound.

| Structure of the synergists (III) | (S) kg/ha | (H) kg/ha | % damage in the case of *Ipomoea hederacea* H | S | H + S |
|---|---|---|---|---|---|
| (1) 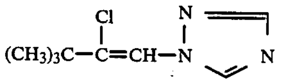 | 0.3 | 0.07 | 10 | — | 90 |
| | 1.0 | 0.07 | 10 | 0 | 70 |
| (6) 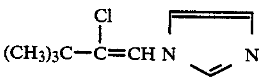 | 0.3 | 0.1 | 10 | — | 30 |
| | 2.0 | 0.1 | 10 | 0 | 100 |
| (3) 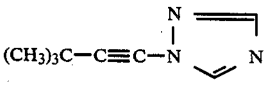 | 0.3 | 0.1 | 10 | — | 80 |
| | 2.0 | 0.1 | 10 | 10 | 100 |
| (8) 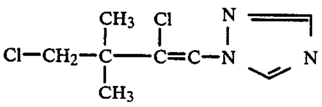 | 0.3 | 0.1 | 10 | — | 90 |
| | 2.0 | 0.1 | 10 | 0 | 90 |
| (7) 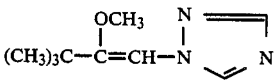 | 0.3 | 0.1 | 10 | — | 50 |
| | 2.0 | 0.1 | 10 | 0 | 60 |
| (2) 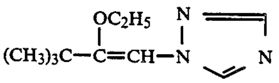 | 0.3 | 0.1 | 10 | — | 30 |
| | 2.0 | 0.1 | 10 | 0 | 60 |
| (10) 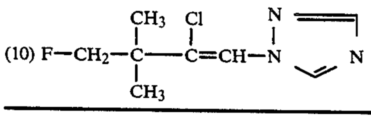 | 0.3 | 0.1 | 10 | — | 90 |
| | 2.0 | 0.1 | 10 | 0 | 100 |

In the following use examples (B) and (C), the synergistic activity of the compounds of the formula (I) according to the invention in combination with arthropodicides are to be illustrated.

Examples of arthropodicides which can be used according to the invention are shown below:

(A)
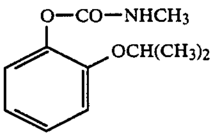
(Propoxur)
(B)
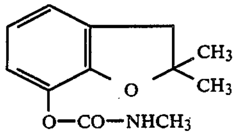
(carbofuran)
(C)
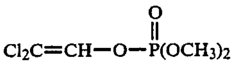
(DDVP)
(D)
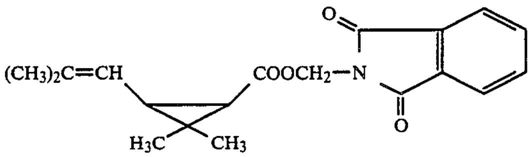
(tetramethrin)
(E)
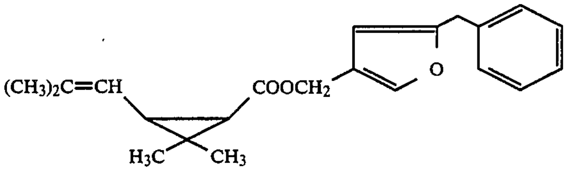
(Desmethrin)
(F)
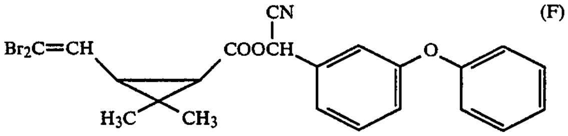
(deltamethrin)
(G)
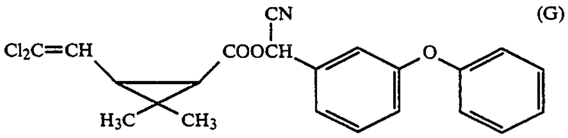
(cypermethrin)
(H)
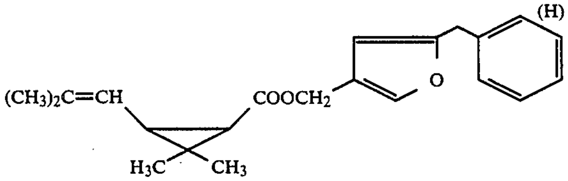
(bioresmethrin)
-continued
(I)
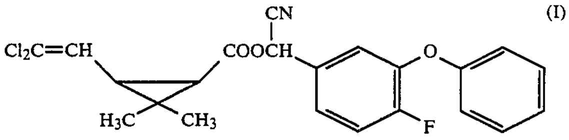
(cyfluthrin)
Examples of insecticide synergists which can be used according to the invention are shown below:
| Synergist No. | Formula | Compound from preparation example No. |
|---|---|---|
| (1) | 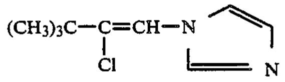 | 6 |
| (2) | 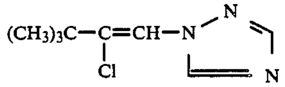 | 1 |
| (3) | 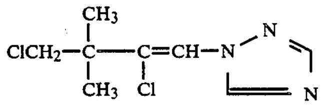 | 8 |
| (4) | 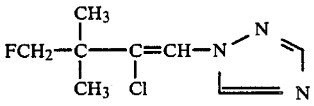 | 10 |
| (5) | 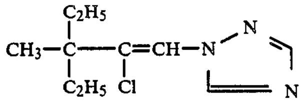 | 16 |
| (6) | 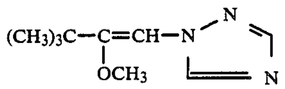 | 7 |
| (7) | 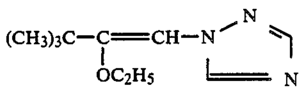 | 2 |
| (8) | 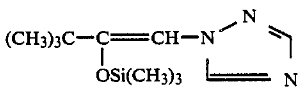 | 11 |
| (9) | 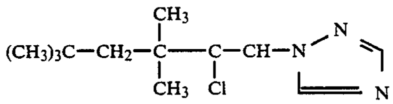 | 17 |
| (10) | 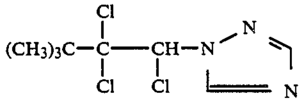 | 4 |
| (11) | 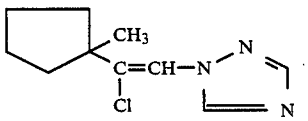 | 15 |

-continued

| Synergist No. | Formula | Compound from preparation example No. |
|---|---|---|
| (12) | 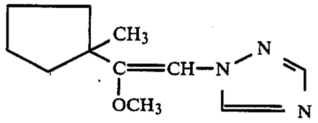 | 12 |
| (13) | 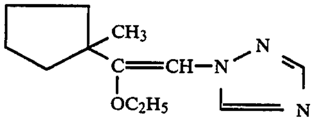 | 13 |
| (14) | 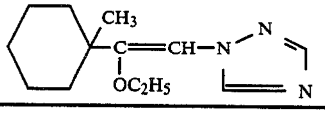 | 14 |

USE EXAMPLE B (insecticide synergism)

$KT_{50}$ aerosol test

Test insects: *Musca domestica* ♂♂, Weymanns strain (resistant to carbamates and phosphates)

Solvent: acetone

To prepare a suitable preparation of active compound, the active compounds, synergists and active compound/synergist mixtures are dissolved in the solvent.

Three wire cages each containing 20 test insects are suspended in the center of a gas-tight 1 $m^3$ glass chamber. After resealing the chamber, 2 ml of the preparation of active compound are sprayed into it. The condition of the test insects is continuously monitored from one outside through the glass walls, and the time required for a 50% knock-down effect ($KT_{50}$) on the insects is determined. If no $KT_{50}$ is reached after 60 minutes, the % of knocked-down insects is determined.

The active compounds, active compound amounts and times at which a 50% knock-down action is present and the % of insects knocked-down (K.D.) after 60 minutes can be seen from the following table:

TABLE B $KT_{50}$ aerosol test with phosphate- and carbamate-resistant male *Musca domestica* (Weymanns strain)

| Active compounds/synergists | | | Concentration in mg/$m^3$ of active compounds + synergists | | | $KT_{50}$ within 60 minutes (% K.D. after 60 minutes) | |
|---|---|---|---|---|---|---|---|
| A | | | 20 | | | none | (60' = 2%) |
| B | | | 10 | | | none | (60' = 25%) |
| C | | | 10 | | | 23' | |
| | | | 5 | | | 36' | |
| | | 1 | | | 20 | none | (60' = 0%) |
| | | 2 | | | 20 | none | (60' = 0%) |
| | | 3 | | | 20 | none | (60' = 0%) |
| | | 4 | | | 20 | none | (60' = 0%) |
| | | 5 | | | 20 | none | (60' = 0%) |
| | | 6 | | | 20 | none | (60' = 0%) |
| | | 7 | | | 20 | none | (60' = 0%) |
| | | 8 | | | 20 | none | (60' = 0%) |
| | | 9 | | | 20 | none | (60' = 0%) |
| | | 10 | | | 20 | none | (60' = 0%) |
| | | 11 | | | 20 | none | (60' = 0%) |
| | | 12 | | | 20 | none | (60' = 0%) |
| | | 13 | | | 20 | none | (60' = 0%) |
| | | 14 | | | 20 | none | (60' = 0%) |
| A | + | 1 | 10 | + | 10 | 45' | |
| A | + | 2 | 10 | + | 10 | 33' | |
| A | + | 3 | 10 | + | 10 | 36' | |
| A | + | 4 | 10 | + | 10 | 31' | |
| A | + | 5 | 10 | + | 10 | 33' | |
| A | + | 6 | 10 | + | 10 | 38' | |
| A | + | 7 | 10 | + | 10 | 47' | |
| A | + | 8 | 10 | + | 10 | 49' | |
| A | + | 9 | 10 | + | 10 | 43' | |
| A | + | 10 | 10 | + | 10 | 35' | |
| A | + | 11 | 10 | + | 20 | 36' | |
| A | + | 11 | 10 | + | 10 | 36' | |
| A | + | 11 | 10 | + | 8 | 37' | |
| A | + | 11 | 10 | + | 5 | 37' | |
| A | + | 11 | 10 | + | 2 | 38' | |
| A | + | 11 | 10 | + | 1 | 46' | |
| A | + | 12 | 10 | + | 10 | 32' | |
| A | + | 13 | 10 | + | 10 | 33' | |
| A | + | 14 | 10 | + | 10 | 38' | |
| B | + | 11 | 10 | + | 10 | 22' | |
| B | + | 11 | 10 | + | 5 | 22' | |
| B | + | 11 | 10 | + | 2 | 26' | |
| B | + | 11 | 10 | + | 1 | 26' | |
| C | + | 11 | 10 | + | 20 | 13' | |
| C | + | 11 | 10 | + | 10 | 15' | |
| C | + | 11 | 10 | + | 5 | 15' | |

USE EXAMPLE C (insecticide synergism)

$KT_{50}$ aerosol test

Test insects: *Musca domestica* ♂♂, Hans strain (resistant to pyrethroids)

Solvent: acetone

To prepare a suitable preparation of active compound, the active compounds, synergists and active compound/synergist mixtures are dissolved in the solvent.

Three wire cages each containing 20 test insects are suspended in the center of a gas-tight 1 $m^3$ glass chamber. After resealing the chamber, 2 ml of the preparation of active compound are sprayed into it. The condition of the test insects is continuously monitored from the outside through the glass walls, and the time required for a 50% knock-down effect ($KT_{50}$) on the insects is determined. If no $KT_{50}$ is reached after 60 minutes, the % of knocked-down animals is determined.

The active compounds, active compound amounts and times at which a 50% knock-down action is present and the % of insects knocked-down (K.D.) after 60 minutes can be seen from the following table:

TABLE C

| KT50 aerosol test with pyrethroid-resistant male *Musca domestica* (Hans strain) | | | | | | | |
|---|---|---|---|---|---|---|---|
| Active compounds/synergists | | | Concentration in mg/$m^3$ of active compounds + synergists | | | $KT_{50}$ within 60 minutes (% K.D. after 60 minutes) | |
| D | | | 10 | | | none | (60′ = 0%) |
| E | | | 20 | | | none | (60′ = 30%) |
| F | | | 4 | | | none | (60′ = 22%) |
| G | | | 4 | | | none | (60′ = 0%) |
| H | | | 10 | | | none | (60′ = 0%) |
| I | | | 2 | | | 52′ | |
| | | 1 | | | 20 | none | (60′ = 0%) |
| | | 2 | | | 20 | none | (60′ = 0%) |
| | | 3 | | | 20 | none | (60′ = 0%) |
| | | 4 | | | 20 | 43′ | |
| | | 5 | | | 20 | none | (60′ = 0%) |
| | | 6 | | | 20 | 42′ | |
| | | 7 | | | 20 | 34′ | |
| | | 8 | | | 20 | none | (60′ = 20%) |
| | | 9 | | | 20 | none | (60′ = 0%) |
| | | 10 | | | 20 | none | (60′ = 0%) |
| | | 11 | | | 20 | none | (60′ = 15%) |
| | | 12 | | | 20 | none | (60′ = 0%) |
| | | 13 | | | 20 | none | (60′ = 0%) |
| | | 14 | | | 20 | none | (60′ = 0%) |
| D | + | 11 | 10 | + | 10 | 41′ | |
| E | + | 11 | 10 | + | 10 | 44′ | |
| E | + | 11 | 10 | + | 5 | 42′ | |
| F | + | 11 | 4 | + | 20 | 14′ | |
| F | + | 11 | 4 | + | 10 | 10′ | |
| F | + | 11 | 4 | + | 5 | 19′ | |
| F | + | 11 | 4 | + | 2 | 21′ | |
| F | + | 11 | 4 | + | 1 | 30′ | |
| G | + | 11 | 4 | + | 10 | 40′ | |
| H | + | 11 | 10 | + | 20 | 40′ | |
| H | + | 11 | 10 | + | 10 | 53′ | |
| I | + | 1 | 2 | + | 2 | 25′ | |
| I | + | 2 | 2 | + | 2 | 43′ | |
| I | + | 3 | 2 | + | 2 | 45′ | |
| I | ° | 4 | 2 | + | 2 | 47′ | |
| I | + | 8 | 2 | + | 2 | 17′ | |
| I | + | 9 | 2 | + | 2 | 38′ | |
| I | + | 10 | 2 | + | 2 | 40′ | |
| I | + | 11 | 2 | + | 10 | 32′ | |
| I | + | 11 | 2 | + | 8 | 32′ | |
| I | + | 11 | 2 | + | 4 | 34′ | |
| I | + | 11 | 2 | + | 2 | 48′ | |
| I | + | 11 | 2 | + | 1 | 36′ | |
| I | + | 12 | 2 | + | 2 | 36′ | |
| I | + | 13 | 2 | + | 2 | 33′ | |

It will be appreciated that the instant specification and examples are set forth by way of illustration and not limitation, and that various modifiations and changes may be made without departing from the spirit and scope of the present invention.

What is claimed is:

1. An insecticidal composition comprising an insecticidally effective amount of an insecticide and a synergistically effective amount of a halogenoalkyl-, alkenyl- or alkinyl-azole of the formula

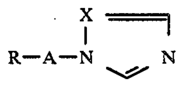

in which

X represents a nitrogen atom or a CH grouping,

R represents optionally halogen-substituted tert.-alkyl having 4 to 8 carbon atoms, or cycloalkyl having 3 to 6 carbon atoms, which is optionally substituted by alkyl having 1 to 4 carbon atoms and/or by halogen, and A represents one of the groupings —C≡C—,

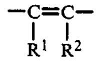 or 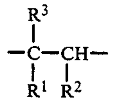

in which $R^1$ represents halogen, alkoxy having 1 to 4 carbon atoms, or trimethylsilyloxy, $R^2$ represents hydrogen or halogen, and $R^3$ represents halogen, or an acid or metal salt addition product thereof.

2. A composition according to claim 1, in which

R represents tert.-alkyl, having 4 to 8 carbon atoms, which is optionally substituted by chlorine and/or fluorine, or represents cyclopropyl, cyclopentyl or cyclohexyl, each of which is optionally substituted by chlorine, methyl, ethyl and/or isopropyl, and A represents the grouping —C≡C—, or A represents the grouping

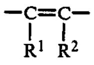

in which (a)

$R^1$ represents chlorine, methoxy, ethoxy or trimethylsilyloxy, and $R^2$ represents hydrogen, or (b)

$R^1$ and $R^2$ represent chlorine or

A represents the grouping

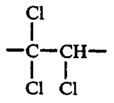

in which $R^1$, $R^2$ and $R^3$ represent chlorine.

3. A composition according to claim 1, wherein the synergist is 2-chloro-3,3-dimethyl-1-(1,2,4-triazol-1-yl)-but-1-ene of the formula

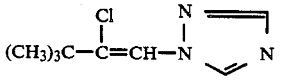

or an addition product thereof with an acid or metal salt.

4. A composition according to claim 1, wherein the synergist is 3,3-dimethyl-1-(1,2,4-triazol-1-yl)-but-1-ine of the formula

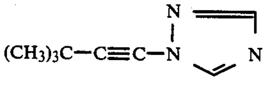

or an addition product thereof with an acid or metal salt.

5. A composition according to claim 1, wherein the synergist is 2-chloro-3-chloromethyl-3-methyl-1-(1,2,4-triazol-1-yl)-but-1-ene of the formula

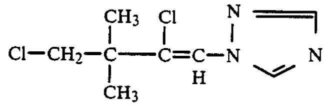

or an addition product thereof with an acid or metal salt.

6. A composition according to claim 1, wherein the synergist is 2-chloro-3-fluoromethyl-3-methyl-1-(1,2,4-triazol-1-yl)-but-1-ene of the formula

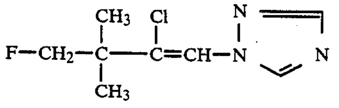

or an addition product thereof with an acid or metal salt.

7. A composition according to claim 1, wherein the synergist is 2-chloro-3,3-trimethylene-1-(1,2,4-triazol-1-yl)-but-1-ene of the formula

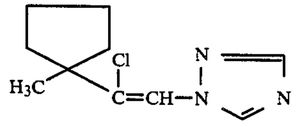

or an addition product thereof with an acid or metal salt.

8. In the combating of insects by applying an insecticide to such insects or to a locus from which it is desired to exclude such insects, the improvement which comprises also applying a synergistically effective amount of a halogenoalkyl-, alkenyl- or alkinyl-azole of the formula

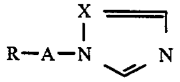

in which

X represents a nitrogen atom or a CH grouping,

R represents optionally halogen-substituted tert.-alkyl having 4 to 8 carbon atoms, or cycloalkyl having 3 to 6 carbon atoms, which is optionally substituted by alkyl having 1 to 4 carbon atoms and/or by halogen, and A represents one of the groupings —C≡C—,

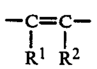 or 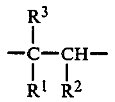

in which $R^1$ represents halogen, alkoxy having 1 to 4 carbon atoms, or trimethylsilyloxy, $R^2$ represents hydrogen or halogen, and $R^3$ represents halogen, or an acid or metal salt addition product thereof.

9. The method according to claim 8, wherein the synergist is 2-chloro-3,3-dimethyl-1-(1,2,4-triazol-1-yl)-but-1-ene, 3,3-dimethyl-1-(1,2,4-triazol-1-yl)-but-1-ine, 2-chloro-3-chloromethyl-3-methyl-1-(1,2,4-triazol-1-yl)-but-1-ene, 2-chloro-3-fluoromethyl-3-methyl-1-(1,2,4-triazol-1-yl)-but-1-ene, or 2-chloro-3,3-trimethylene-1-(1,2,4-triazol-1-yl)-but-1-ene, or an addition product thereof with an acid or metal salt.

* * * * *

UNITED STATES PATENT AND TRADEMARK OFFICE
CERTIFICATE OF CORRECTION

PATENT NO. : 4,783,474

DATED : Nov. 8, 1988

INVENTOR(S) : Kraatz et al.

It is certified that error appears in the above-identified patent and that said Letters Patent is hereby corrected as shown below:

| | |
|---|---|
| Col. 5, line 47 | Insert --alkenyl, $C_3$-$C_5$- alkinyl or $C_3$-$C_6$- -- after "$C_3$-$C_5$-" |
| Col. 5, line 61 | Insert --5-- after "C" in sixth instance |
| Col. 8, line 44 | Correct spelling of --cyclopropane-- |
| Col. 10, line 44 | Correct spelling of --with-- |
| Col. 11, line 33 | Delete "(A)" and substitute --(a)-- |
| Col. 12, line 39 | Correct spelling of --variant-- |
| Col. 25, line 12 | Correct spelling of --Convolvulus- |
| Col. 25, line 28 | Correct spelling of --Portulaca-- |
| Col. 26, line 55 | Correct spelling of --Periplaneta-- |
| Col. 27, line 39 | Correct spelling of --Amphimallon solstitialis-- |
| Col. 27, line 58 | Correct spelling of --Chorioptes-- |
| Col. 29, line 59 | Correct spelling of --mixture-- |
| Col. 29, line 61 | Correct spelling of --dissolved-- |
| Col. 34, line 22 | Insert --,-- after "2" |
| Col. 35, line 65 | Insert --(1R-trans)-- under right portion of formula |

UNITED STATES PATENT AND TRADEMARK OFFICE

CERTIFICATE OF CORRECTION

PATENT NO. : 4,783,474
DATED : Nov. 8, 1988
INVENTOR(S) : Kraatz et al.

It is certified that error appears in the above-identified patent and that said Letters Patent is hereby correctea as shown below:

Col. 38, line 17 — Delete "one" and substitute --the--

Signed and Sealed this

Twenty-second Day of August, 1989

Attest:

DONALD J. QUIGG

Attesting Officer — Commissioner of Patents and Trademarks